US012594425B2

(12) United States Patent
Wolf, II

(10) Patent No.: US 12,594,425 B2
(45) Date of Patent: Apr. 7, 2026

(54) APPARATUS AND METHOD FOR REDUCING THE EFFECT OF LEAD MIGRATION DURING SPINAL CORD STIMULATION

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 545 days.

(21) Appl. No.: 17/646,697

(22) Filed: Dec. 31, 2021

(65) Prior Publication Data

US 2023/0211163 A1     Jul. 6, 2023

(51) Int. Cl.
*A61N 1/36*        (2006.01)
*A61N 1/05*        (2006.01)

(52) U.S. Cl.
CPC ..... *A61N 1/36139* (2013.01); *A61N 1/36062* (2017.08); *A61N 1/36125* (2013.01); *A61N 1/36167* (2013.01); *A61N 1/0551* (2013.01); *A61N 1/36071* (2013.01)

(58) Field of Classification Search
CPC ............ A61N 1/36125; A61N 1/36071; A61N 1/36139; A61N 1/36062; A61N 1/36185; A61N 1/0551; A61N 1/36167
See application file for complete search history.

(56) References Cited

U.S. PATENT DOCUMENTS

| | | | |
|---|---|---|---|
| 6,356,792 B1 | 3/2002 | Errico et al. | |
| 9,579,222 B2 | 2/2017 | Brånemark et al. | |
| 9,737,233 B2 | 8/2017 | Londot | |
| 10,035,019 B2 | 7/2018 | Wolf, II | |
| 10,154,866 B2 | 12/2018 | Kim | |
| 2006/0247735 A1* | 11/2006 | Honert | A61N 1/323 607/57 |
| 2014/0163639 A1* | 6/2014 | Zhu | A61B 5/7221 607/46 |
| 2015/0360031 A1* | 12/2015 | Bornzin | A61N 1/36139 607/62 |
| 2016/0206883 A1* | 7/2016 | Bornzin | A61N 1/36182 |
| 2021/0001114 A1 | 1/2021 | Wolf, II | |
| 2021/0001115 A1 | 1/2021 | Wolf, II | |
| 2021/0001130 A1 | 1/2021 | Wolf, II | |
| 2022/0023620 A1 | 1/2022 | Wolf, II | |

\* cited by examiner

*Primary Examiner* — Jennifer Pitrak McDonald
*Assistant Examiner* — Christine Sison
(74) *Attorney, Agent, or Firm* — Schultz & Associates, P.C.

(57) ABSTRACT

In the present invention, an IPG incorporates electrical resistivity monitoring with a reflectometry trigger. The IPG is configured to determine both optically and electrically if migration occurs between the electrodes. If the light intensity variation in the optical trigger is greater than an optical threshold value, then the system will pause stimulation and conduct a resistivity test. A resistivity test is also conducted periodically in the absence of the reflectometry trigger to verify that no lead migration has occurred. The stimulation signal is automatically adjusted if a variation in resistivity values is detected above a resistivity threshold value. The resistivity threshold value is set above the normal variation that occurs due to routine movement of the spinal cord in the spinal canal.

17 Claims, 14 Drawing Sheets

700

701 — OPTICAL SIGNAL STRENGTH TEST

702 — STORE BASELINE VALUES

703 — CONDUCT INITIAL RESISTIVITY TEST

704 — STORE BASELINE VALUES

706 — SET RESISTIVITY VARIATION THRESHOLD

708 — SET LIGHT INTENSITY VARIATION THRESHOLD

709 — SET STIMULATION EPOCHS

710 — SET RELAY 1

711 — SET RELAY 2

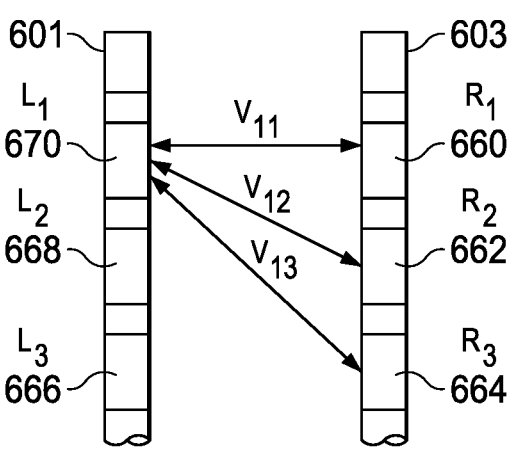
FIG. 9B
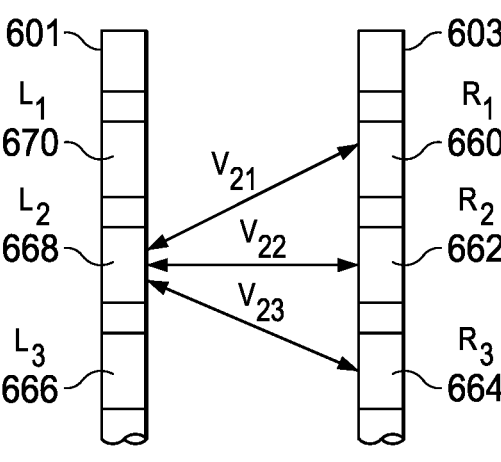
FIG. 9C
FIG. 9D

APPARATUS AND METHOD FOR REDUCING THE EFFECT OF LEAD MIGRATION DURING SPINAL CORD STIMULATION

FIELD OF THE INVENTION

The present invention relates generally to spinal cord stimulation ("SCS") and a technique for automatic adjustments of SCS using near-infrared (NIR) reflectometry and electrical resistivity.

BACKGROUND OF THE INVENTION

Chronic pain may arise from a variety of conditions, most notably from nerve injury as in the case of neuropathic pain, or from chronic stimulation of mechanical nociceptors such as with spinal pain. Functional ability may be severely impacted by pain, which often is refractory to pharmacological and surgical treatment. In such cases, SCS can be an effective treatment for pain by modulating physiological transmission of pain signals from the periphery to the brain. This may be achieved by applying electrical impulses to the spinal cord via an electrode array placed in the dorsal epidural space.

In FIG. 1, spinal column 100 is shown to have a number of vertebrae, categorized into four sections or types: lumbar vertebrae 102, thoracic vertebrae 104, cervical vertebrae 106 and sacral vertebrae 108. Cervical vertebrae 106 include the 1st cervical vertebra (C1) through the 7th cervical vertebra (C7). Just below the 7th cervical vertebra is the first of twelve thoracic vertebrae 104 including the 1st thoracic vertebra (T1) through the 12th thoracic vertebra (T12). Just below the 12th thoracic vertebrae 104, are five lumbar vertebrae 102 including the 1st lumbar vertebra (L1) through the 5th lumbar vertebra (L5), the 5th lumbar vertebra being attached to sacral vertebrae 108 (S1 to S5), sacral vertebrae 108 being naturally fused together in the adult. Electrical lead 110 is implanted between thoracic vertebrae 104, such that electrical lead 110 may deliver an electric current to spinal root nerves. Electrical lead 110 is attached via lead wire 112 to implantable pulse generator ("IPG") 116. IPG 116 has a header 114 that allows lead wire 112 to attach to an IPG, but can be removed to allow IPG 116 to be replaced or serviced without disturbing electrical lead 110. IPG 116 typically is constructed of titanium and acts as a signal to ground 115 for the stimulation signal from the electrodes. Communications and instructions from external controller 117 are usually received by IPG 116, wirelessly from keypad 119.

Referring to FIG. 2, a cross-sectional view of vertebra 200 is shown enclosing spinal cord 202. Surrounding spinal cord 202 is dura 210 that contains cerebrospinal fluid (CSF). The thick oval segment of bone forming the anterior aspect of vertebra 200 is vertebral body 206. Vertebral body 206 is attached to bony vertebral arch 208 through which spinal nerves 214 run. Vertebral arch 208, forming the posterior of vertebra 200, is comprised of two pedicles 216, which are short stout processes that extend from the sides of vertebral body 206 and bilateral laminae 220. The broad flat plates that project from pedicles 216 join in a triangle to form a hollow archway, spinal canal 212. Spinous process 218 protrudes from the junction of bilateral laminae 220. Transverse processes 222 project from the junction of pedicles 216 and bilateral laminae 220. The structures of the vertebral arch protect spinal cord 202 and spinal nerves 214 that run through the spinal canal.

Referring then to FIGS. 2 and 3, percutaneous leads 224A and 224B are implanted in epidural space 204 of between dura 210 and the walls of spinal canal 212. In a preferred embodiment, between two and three percutaneous leads are implanted in the epidural space side-by-side at a predetermined distance apart, adjacent, and generally parallel to, each other. Each percutaneous lead is comprised of an electrode array and, preferably, optical components that accommodate adjustment of the stimulation signal.

The IPG delivers pulses of electrical current to the electrode array, which stimulates targeted neurons within the ascending tracts of the spinal cord and disrupts the perception of pain in target area 226. Precise placement of the percutaneous leads is required to provide optimal stimulation of target area 226. Furthermore, controlling the amplitude of the stimulating electrical current is paramount to success of spinal cord stimulation. Applying inadequate current will fail to depolarize the targeted neurons, rendering the treatment ineffective. Conversely, application of excess current will depolarize the targeted neurons, but also stimulate additional cell populations which renders the perception of a noxious stimulation.

Establishing a consistent, therapeutic, and non-noxious level of stimulation is predicated upon establishing an ideal current density within the spinal cord's targeted neurons. Fundamentally, this should be a simple matter of precise electrode placement and establishing an optimal electrode current given the local bulk conductivity of the surrounding tissues. However, in practice, the optimal electrode current changes as a function of patient position. Consequently, it is preferred to dynamically adjust the electrode stimulation current as a function of distance between the electrode array and the spinal cord. An optical signal can be transmitted into the surrounding tissue and collected by a sensor to calculate the approximate distance between the electrode and the spinal canal. A new level of electrical current is then implemented in the stimulation signal to accommodate for the distance in order to maintain the efficacy of treatment. An example of this technology is shown in U.S. Pat. No. 10,035,019 to Wolf, incorporated herein by reference for all purposes.

One challenge to permanent IPG placement is that the percutaneous leads are susceptible to migration over time. As the leads move, the distance to the targeted spinal cord segment changes, which both diminishes the efficacy of the stimulation technique and can cause other complications necessitating surgical correction of the migration or removal of the electrode array altogether.

The problem of electrode migration has been addressed by other prior art techniques but has not been adequately resolved.

For example, in the prior art, reflectometry only accounts for normal movement of the spinal cord within the spinal canal. Thus, prior art reflectometry cannot account for any angular, lateral, superior, or inferior lead migration. As a result, the stimulation current and amplitude may be adjusted incorrectly resulting in the stimulation epicenter changing from the targeted spinal cord segment, thus causing either noxious or ineffective stimulation.

As another example, prior art techniques have provided a way to secure a percutaneous lead by frictionally engaging the lead surface with an anchoring hook that is driven into the fibrous fascia layer surrounding the nerve root, as disclosed and claimed in U.S. patent application Ser. No. 17/443,174 to Wolf. However, the anchoring hook must pierce the nerve fascia layer which requires surgical skill and care because of the risk of nerve damage.

As another example, U.S. Pat. No. 10,154,866 to Kim discloses a medical insertion apparatus comprised of a nail body implanted in a boney structure. The nail body includes an electrode connected to a lead which runs inside a cavity in the nail. The position of the electrode is fixed at the terminal end of the nail body, requiring the nail body to be located immediately peripheral to the targeted nerve, which is not always possible when targeting the spinal cord. Furthermore, the nail body must be seated perpendicularly to the surrounding bone, prohibiting an electrode position parallel to the spinal cord.

As another example, U.S. Pat. No. 6,356,792 to Errico, et al. discloses an assembly for securing an electrode inside the skull. A skull port member is affixed to the skull. An electrode is placed inside the skull and the connecting lead is run through the skull port member. The electrode is secured by a mechanism that seats in the skull port member and crimps the connecting lead. However, the electrode is susceptible to movement when the operator inserts the lead-locking mechanism into the skull port member and crimps the connecting lead. The nature of the mechanism also limits the size of the assembly, as thinner and lighter materials would be likely to break when crimped in place by the lead locking mechanism. Furthermore, the design is ill-suited for use in the spine, as there is no way to position the electrode perpendicular to the direction of the skull port member, which is desirable for stimulation of spinal nerves.

As yet another example, U.S. Pat. No. 9,737,233 to Londot discloses an assembly having a pedicle screw with an electrically-conductive longitudinal member that is used to propagate a signal along the exterior of the pedicle screw. However, the assembly does not allow for placement of the electrode beyond the pedicle screw and limits locations to which electrical stimulation can be applied.

As another example, U.S. Pat. No. 9,579,222 to Branemark, et al. discloses a percutaneous gateway for transmission of signals from a patient's nervous system to a robotic prosthesis. The system discloses an apparatus for mounting a prosthesis and preserving the percutaneous transmission of signals with appropriate seals to prevent infection after long-term use, as well as use with stimulating electrodes that may optionally be implanted. However, the system does not disclose a method for locating the electrodes relative to targeted nerves, anchoring the position of the electrodes, or implantation in the spine.

In all cases, lead migration may still occur. Hence, there remains a need for an electrode array and stimulation system that can effectively adjust a stimulation signal to eliminate the effects of undesired lead migration.

SUMMARY OF THE INVENTION

In the present invention, an IPG incorporates electrical resistivity monitoring with a reflectometry trigger. The IPG is configured to determine both optically and electrically if migration occurs between the electrodes. In one embodiment, if the light intensity variation in the optical trigger is greater than an optical threshold value, then the system will pause stimulation and conduct a resistivity test. A resistivity test is also conducted periodically in the absence of the reflectometry trigger to verify that no lead migration has occurred. The stimulation signal is automatically adjusted if a variation in resistivity values is detected above a resistivity threshold value. The resistivity threshold value is set above the normal variation that occurs due to routine movement of the spinal cord in the spinal canal. In a preferred embodiment, the threshold is set to compensate for the transitory sagittal movement of the leads that typically interferes with optimal stimulation signal generation.

A baseline optical value is stored and associated with the optimal placement of the percutaneous leads. Likewise, a set of baseline resistivity values is stored and associated with the optimal placement of the percutaneous leads. Subsequent optical trigger readings and resistivity values are then compared to the baseline values to determine if the leads have migrated. Based on the demarcation from the baseline values, the system then automatically adjusts the stimulation signal to accommodate for the movement and to maintain optimal stimulation of the target spinal cord segment.

BRIEF DESCRIPTION OF THE DRAWINGS

In the detailed description of the preferred embodiments presented below, reference is made to the accompanying drawings.

FIGS. 9B, 9C, and 9D are a schematic drawing of a preferred method for measuring lead position.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness. All tolerances are plus or minus 20% unless otherwise specified.

Figure 1:
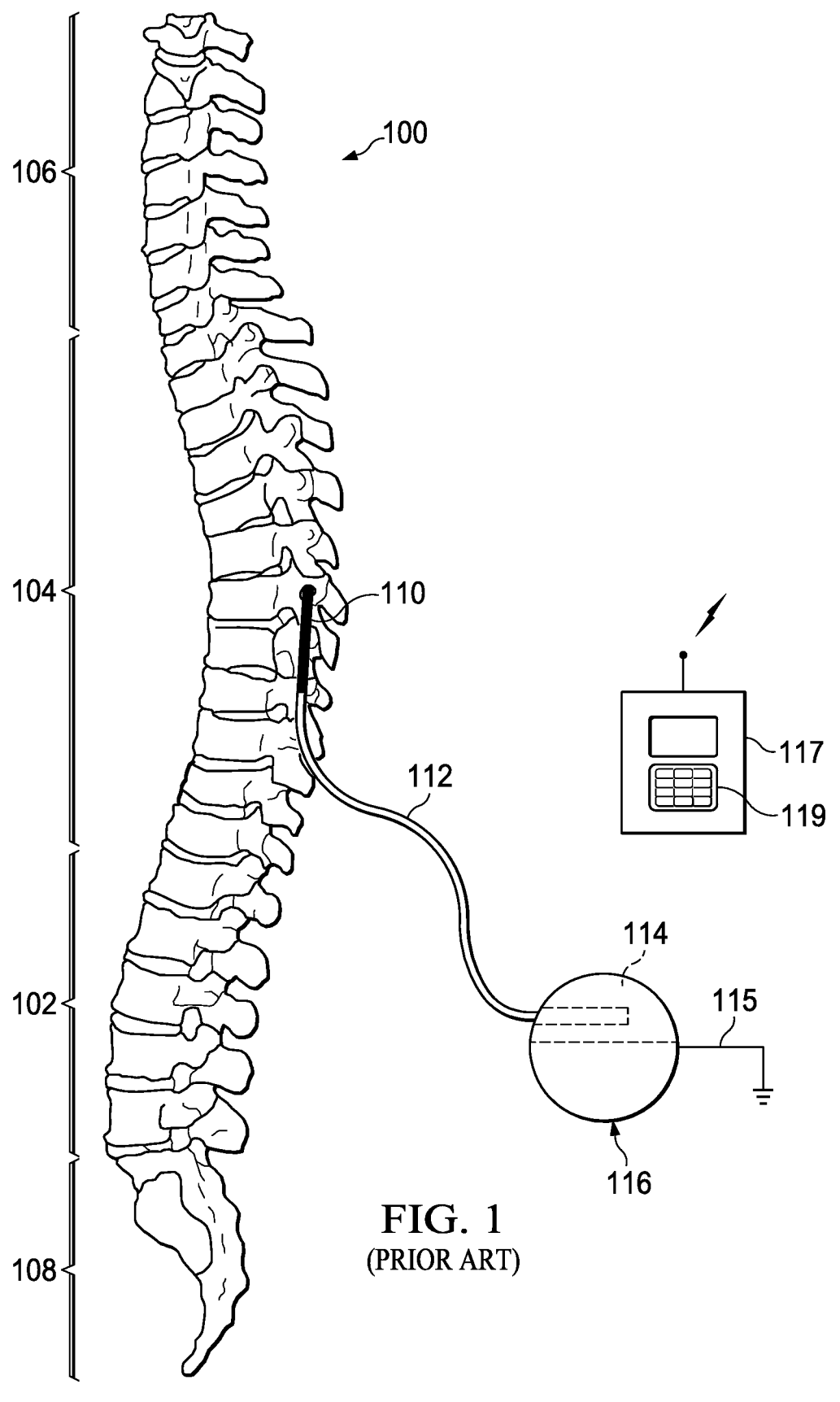
FIG. 1 is a sagittal view of the human spine showing the approximate position of an electrode array for spinal cord stimulation.
Figures 2, 3:
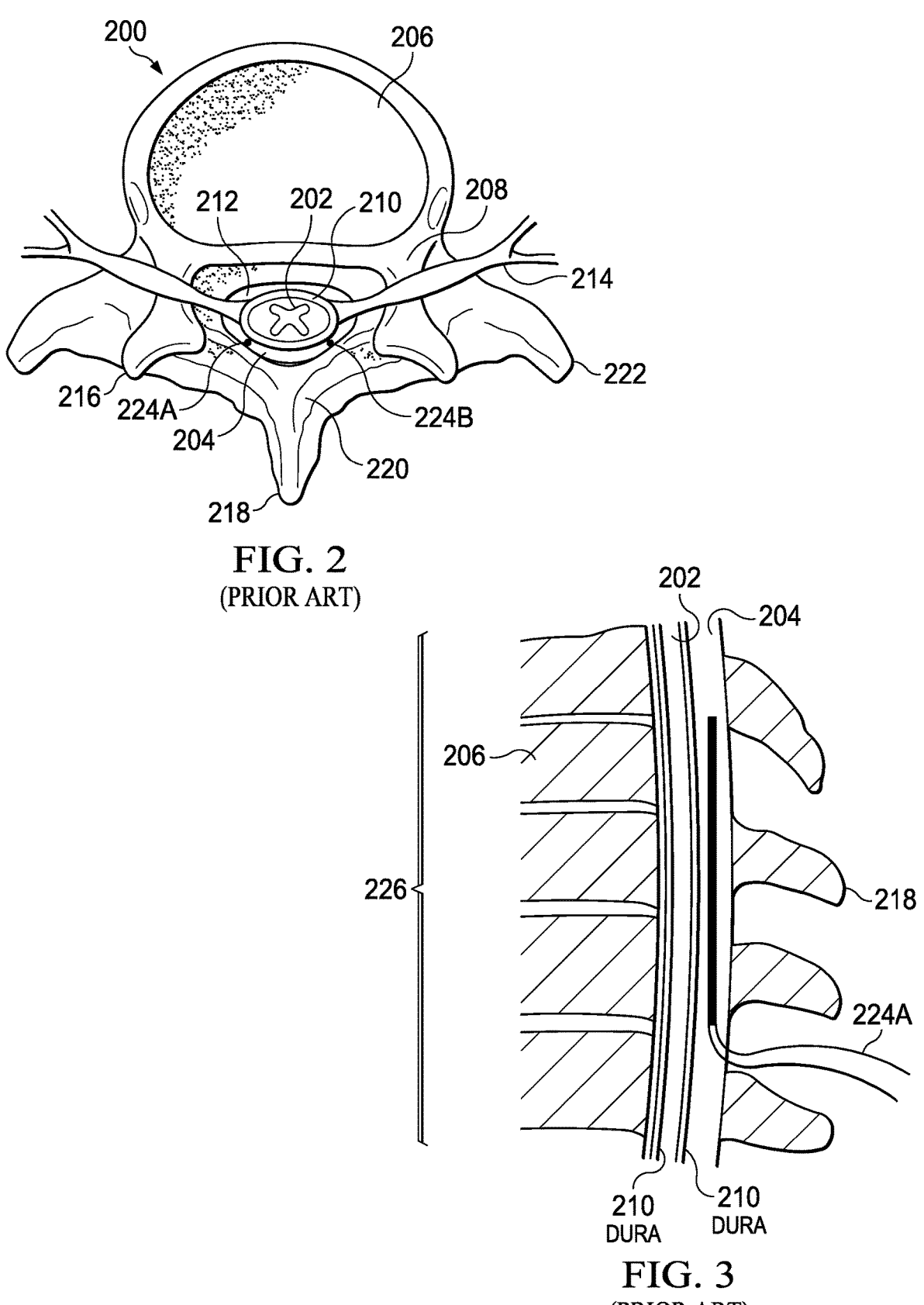
FIG. 2 shows an axial view of a thoracic vertebra indicating the position of the spinal cord and an electrode array for spinal cord stimulation.
FIG. 3 shows a sagittal cross-sectional view of the human spine showing the approximate position of an electrode array for spinal cord stimulation.
Figure 4A:
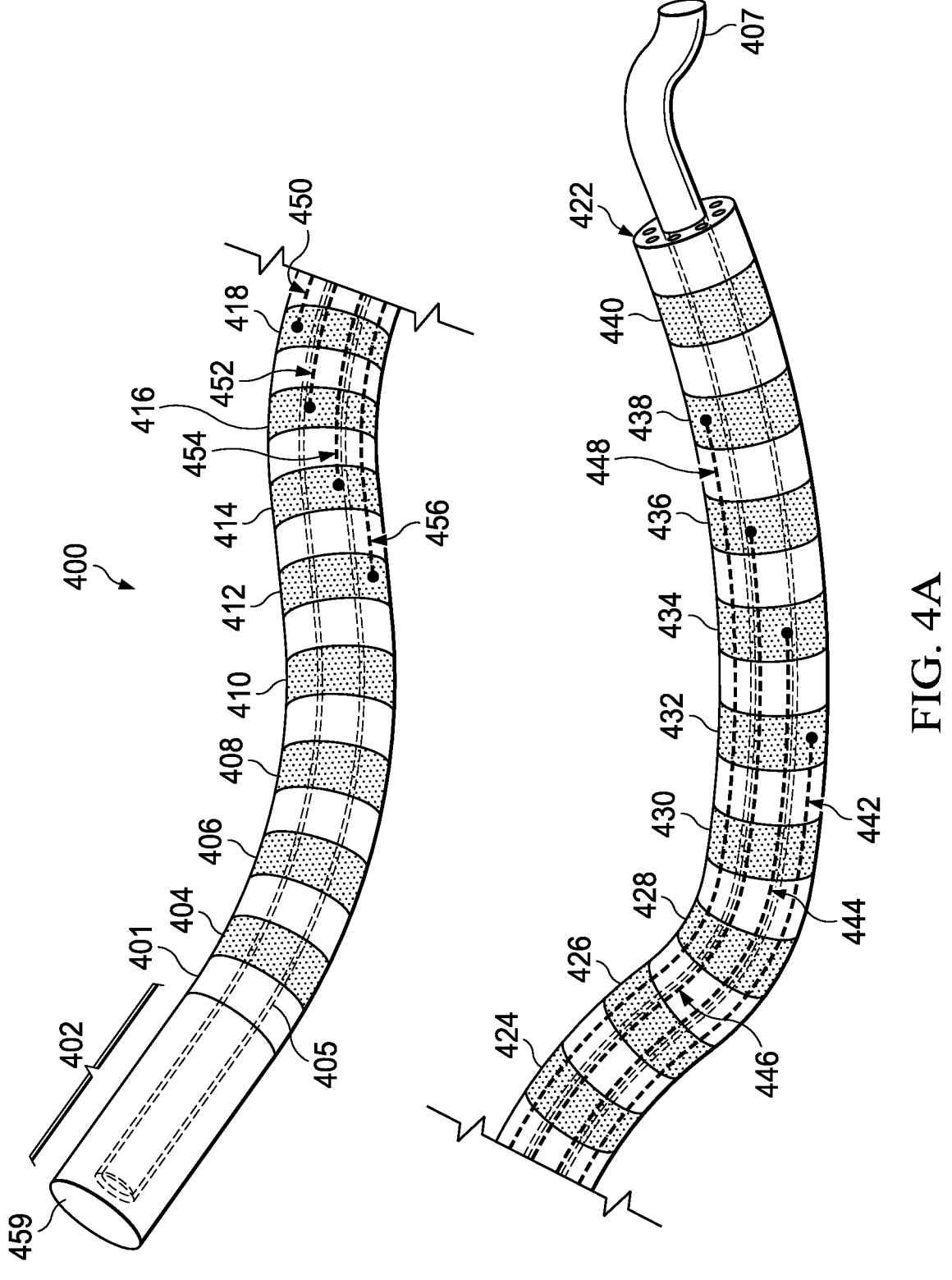
FIG. 4A is a perspective view of a preferred embodiment of a percutaneous lead.
Figure 4B:
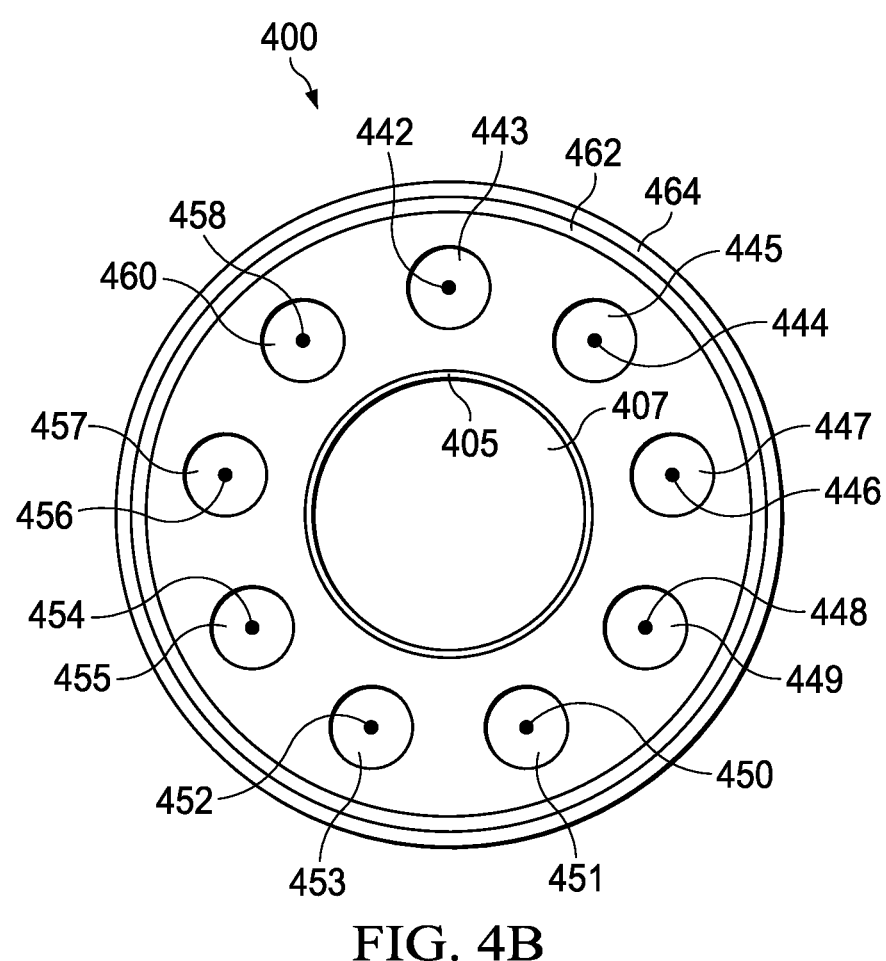
FIG. 4B is a cross-sectional view of a preferred embodiment of a percutaneous lead.

Referring then to FIGS. 4A and 4B, percutaneous lead 400, will be further described. In a preferred embodiment, two (2) identical percutaneous leads, such as percutaneous lead 400, are employed, one implanted on the right, and the other implanted on the left of the spinal cord.

Percutaneous lead 400 is comprised of lead body 401 forming a flexible, generally hollow tube terminated by optical transmission window 402 and anchor ring 440. Optical transmission window 402 includes by internally reflective cap 459. Stylet channel 405 extends from the transmission window to proximal end 422 of the lead body. The stylet channel serves the dual purposes of housing a guide stylet for use during placement of the lead during surgery, and housing optical fiber 407 after surgery.

In a preferred embodiment, lead body 401 is comprised of nine radially positioned lumens, 443, 445, 447, 449, 451, 453, 455, 457 and 460. Conductors 442, 444, 446, 448, 450, 452, 454, and 456, and ground line 458 are located in the lumens.

Conductors 442, 444, 446, 448, 450, 452, 454, and 456 are electrically connected to eight cylindrical proximal metallic contacts 424, 426, 428, 430, 432, 434, 436, and 438. The metallic contacts are fixed to the exterior of the lead body at even axial distances along the lead body and positioned to electrically connect to an IPG header (not shown).

In the same way, the conductors are electrically connected to eight cylindrical distal metallic electrodes 404, 406, 408, 410, 412, 414, 416, 418. The distal electrodes are each permanently fixed to the exterior surface of the lead body at even axial distances along the lead body distal to the optical window.

Ground line 458 extends from proximal end 422 of the lead body to anchor ring 440. The anchor ring is generally cylindrical and is permanently affixed to the exterior of the lead body at proximal end 422. The ground line is selectively connected to the IPG ground through a relay, as will be further described.

In a preferred embodiment the conductors are comprised of MP35N, or another conductive material similarly resistant to corrosion. Each of the conductors connects exactly one proximal contact to a single paired distal electrode. In a preferred embodiment, each of electrodes, and the ground, and are individually addressable by the IPG, as will be further described.

Optionally, the lead body may incorporate non-metallic shielding layer 462, connected to ground line 458, to further enhance MRI capability. In a preferred embodiment, the shielding layer is formed by carbon fibers infused into the surface of the lead body. In another preferred embodiment, low friction layer 464, such as PTFE, is included on the exterior of the lead body to aid in placement of the lead during surgery.

Optical fiber 407 is positioned in stylet channel 405 and extends from proximal end 422 to transmission window 402.

In a preferred embodiment, the percutaneous leads used are those further set out in U.S. Publication Nos. 2021/0001114, 2021/0001115, and 2021/0001130 to Wolf, incorporated herein by reference for all purposes.

Figure 5B:
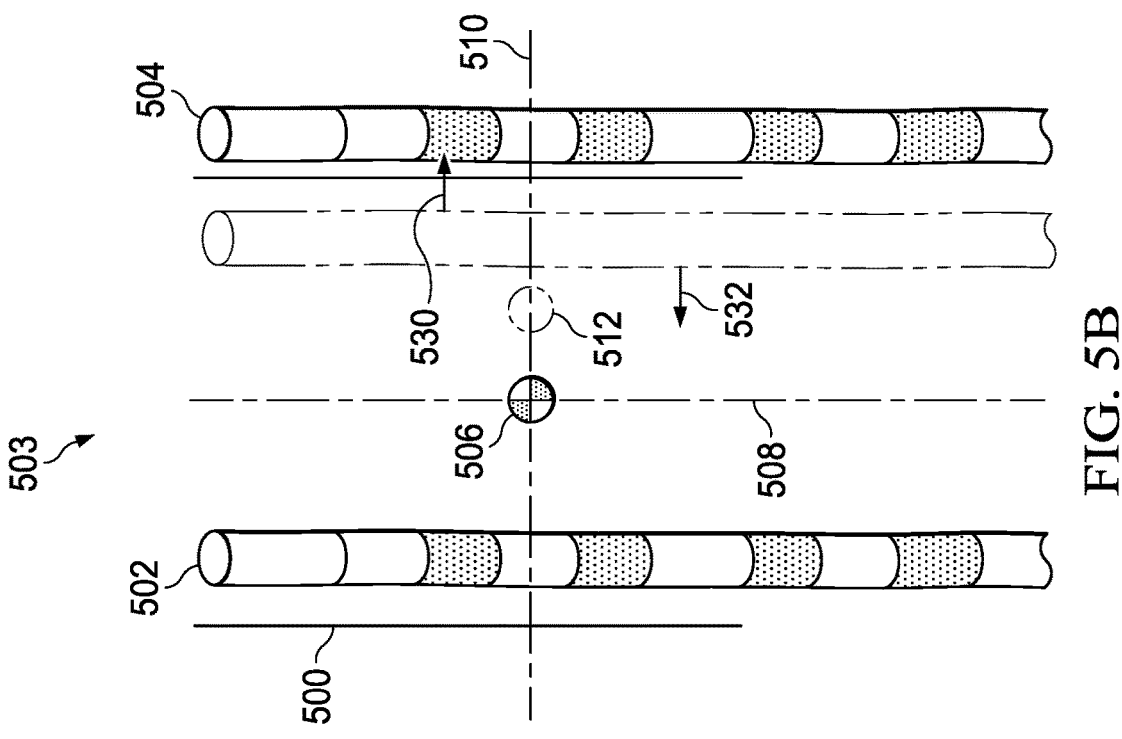
FIGS. 5B, 5C, and 5D show examples of typical modes of lead migration.
Figure 5A:
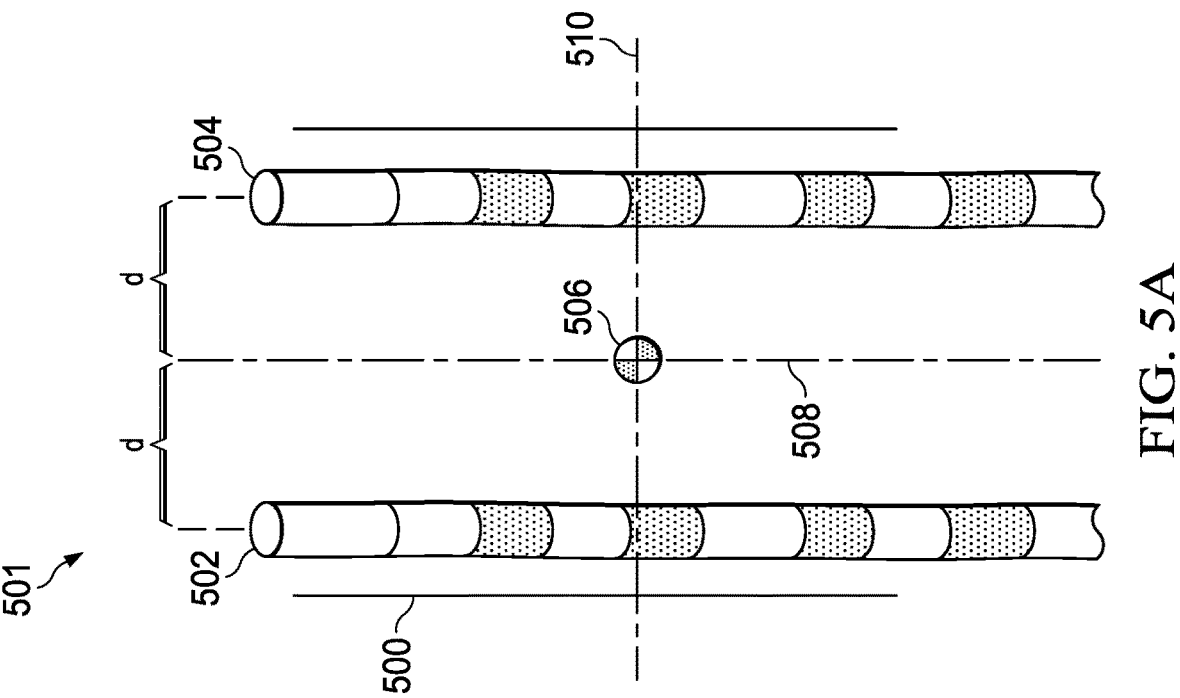
FIG. 5A shows a typical ideal placement of right and left percutaneous leads.

Referring then to FIG. 5A, a preferred positioning 501 of percutaneous leads will be further described.

In a preferred embodiment, percutaneous leads 502 and 504 are each positioned distance "d" from central axis 508 of spinal cord 500. Percutaneous leads 502 and 504 are positioned such that the latitudinal midline of each set of electrodes approximately aligns with horizontal axis 510 of focal point 506. Focal point 506 is the target stimulation region of spinal cord 500. After the percutaneous leads are positioned, the stimulation signal emitted from each electrode is calibrated to focus the optimal amount of electrical stimulus at focal point 506. In this example, focal point 506 is shown along central axis 508, however, it should be appreciated that the target stimulation region may be located in other positions.

Figure 5D:
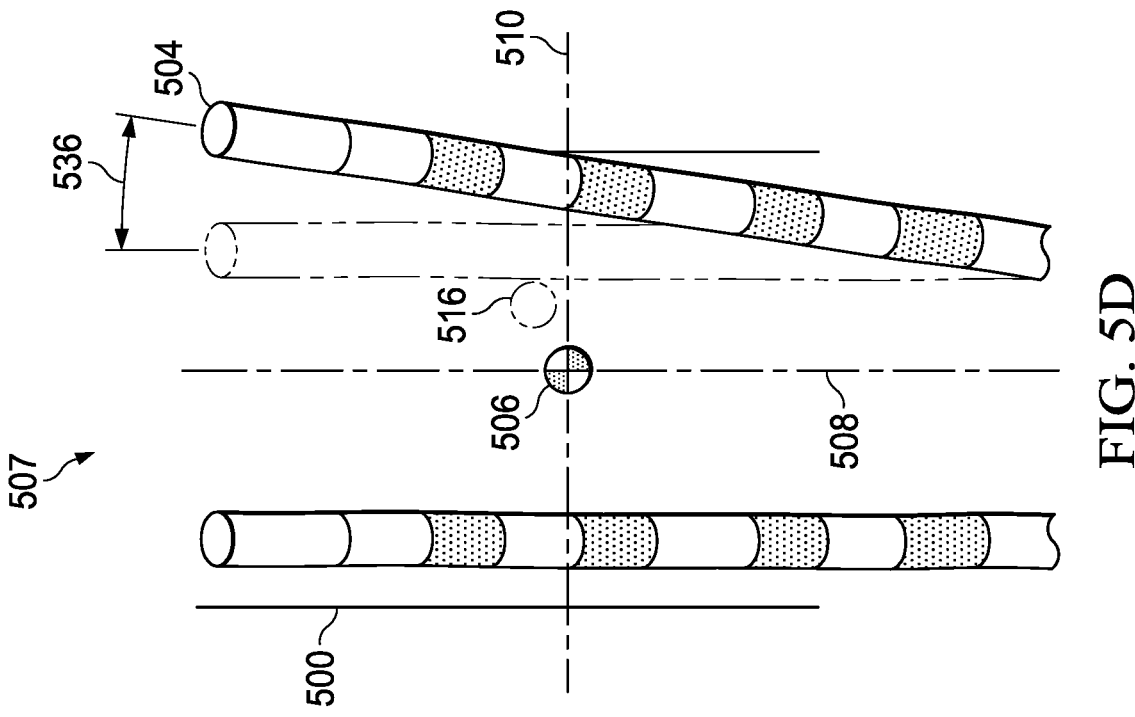
Figure 5C:
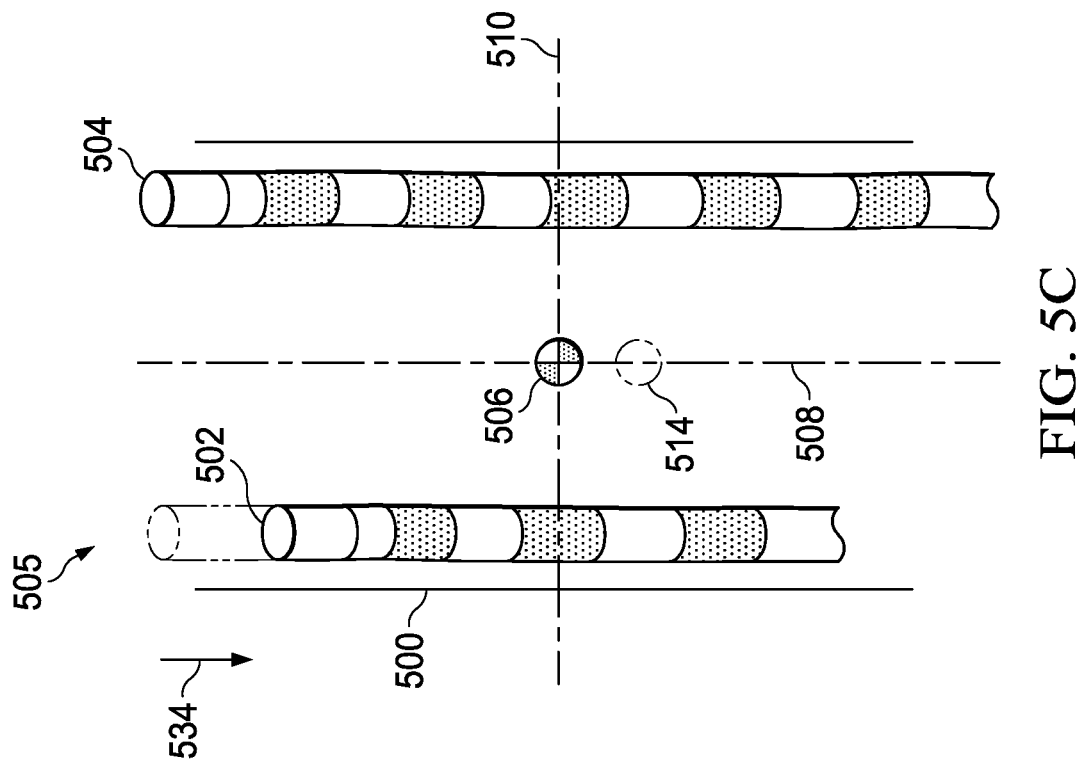

Referring then to FIGS. 5B, 5C, and 5D, exemplary lead migration modes are further described. It should be understood that the leads may migrate in these or any other combination of migration modes or to other locations.

Referring then to FIG. 5B, in exemplary lead migration mode 503, percutaneous lead 504 has migrated laterally away from percutaneous lead 502, as shown by path 530. As a result, the electrical stimulation focal point changes to position 512. As a result, focal point 506 receives ineffective stimulation. Conversely, if a lead uniformly migrates laterally inward, for example along path 532, noxious stimulation may result, at focal point 506.

Referring then to FIG. 5C, in exemplary lead migration mode 505, percutaneous lead 502 has uniformly migrated distally and superiorly, as indicated by arrow 534. As a result, the electrical stimulation focuses at point 514, instead of focal point 506.

Referring then to FIG. 5D, in exemplary lead migration mode 507, percutaneous lead 504 has migrated by angle 536, clockwise, approximately 10°. As a result, the electrical stimulation simultaneously focuses at point 516, instead of focal point 506.

Figure 6B:
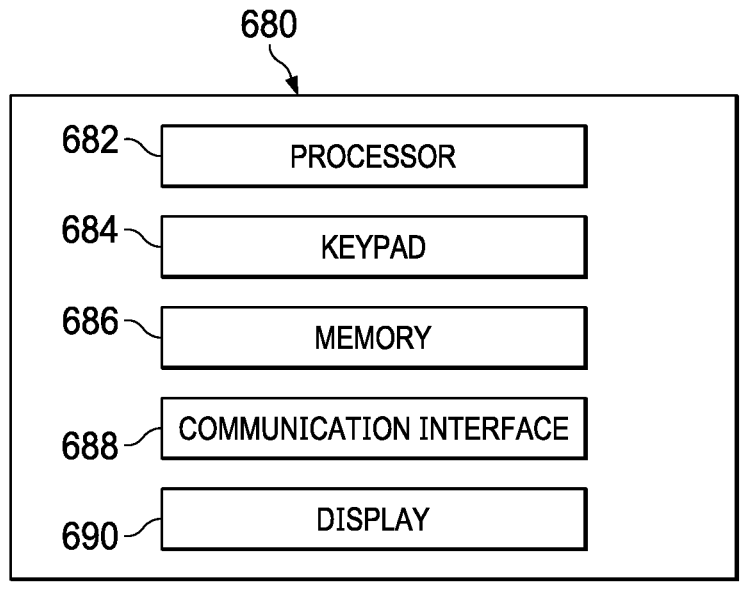
FIG. 6B is an architecture diagram of the components of a preferred embodiment of an IPG controller.
Figure 6A:
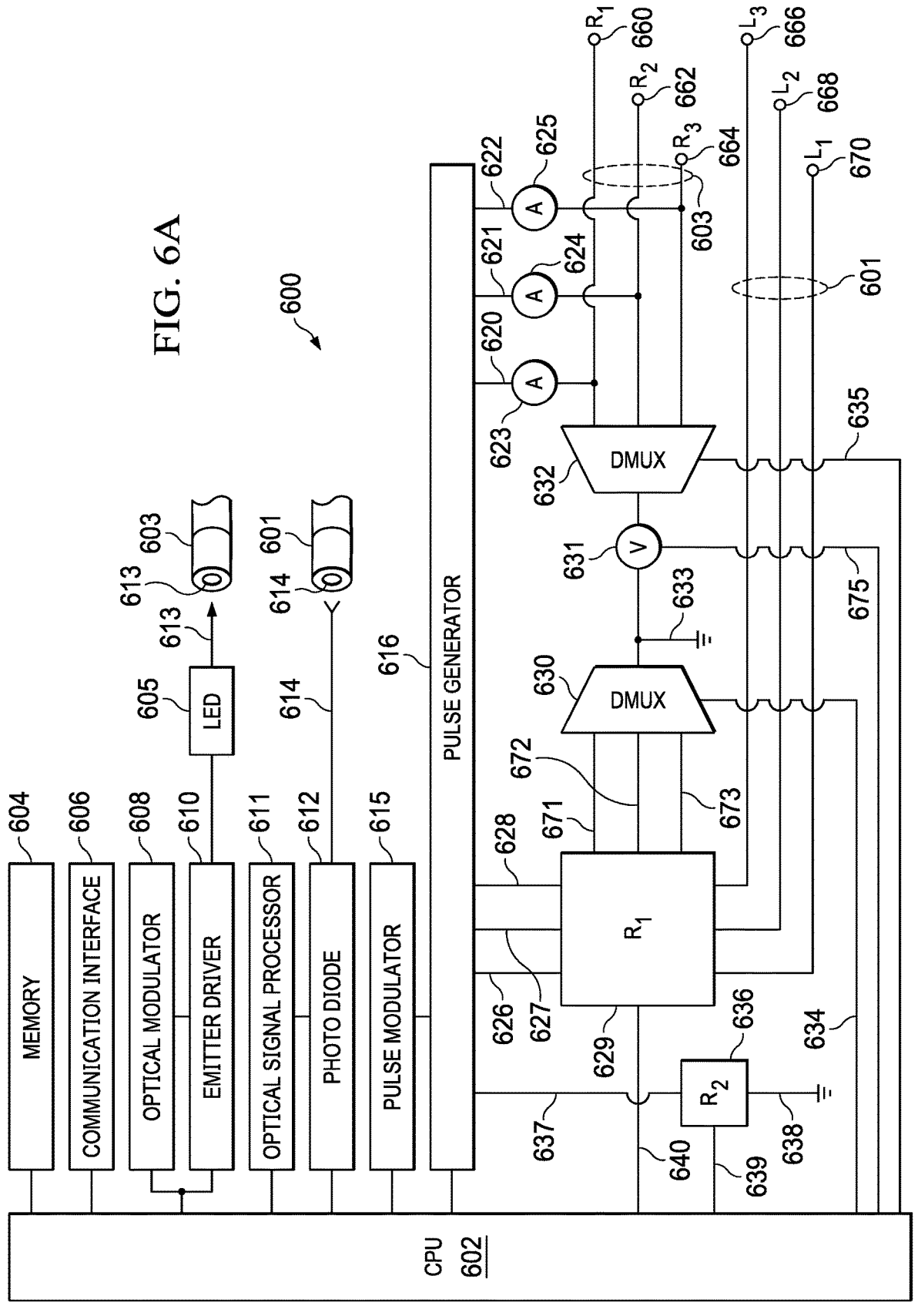
FIG. 6A is a schematic diagram of a preferred embodiment of a pulse generation and optical signal processing unit.

Referring then to FIG. 6A, an architecture diagram of a preferred IPG 600, will be further described.

IPG 600 includes CPU 602 having onboard memory 604. The memory contains a set of instructions that, when executed, cause the CPU to execute functions necessary to send stimulation signals and adjust them according to optical feedback. The instructions also cause the CPU to monitor the placement of the electrodes and automatically correct the stimulation signals, as will be further described.

CPU 602 is also operably connected to communications interface 606. Communications interface 606 sends signals to and receives signals from the master controller wirelessly, as will be further described.

CPU 602 is operatively connected to optical modulator 608 and optical signal processor 611. Optical modulator 608 is connected to emitter driver 610. Emitter driver 610 is connected to LED emitter 605. The LED emitter is optically coupled to optical fiber 613 located in percutaneous lead 603. In a preferred embodiment, the LED emitter operates in the frequency range of about 850 nm to about 2500 nm.

CPU 602 is also connected to optical signal processor 611. Optical signal processor 611 is connected to photodetector 612 that is optically coupled to optical fiber 614, in percutaneous lead 601.

The optical modulator, optical signal processor, emitter driver LED and photo detectors are responsible for sending and receiving spinal cord positioning signals used to adjust the stimulation waveform when the IPG is in use, as more fully described in U.S. Pat. No. 10,035,019 to Wolf, incorporated herein by reference for all purposes.

CPU 602 is also connected to pulse modulator 615 and pulse generator 616. Pulse modulator 615 is connected to pulse generator 616.

In order to generate a pulse to the electrodes for stimulation, the CPU determines pulse width, pulse frequency and pulse amplitude for each the left and right electrodes to create an ideal electrical field at the chosen focal point. The pulse width and frequency are transmitted to pulse modulator 615 which creates a modified square wave signal. The modified square wave signal is passed to pulse generator 616. Pulse generator 616 then amplifies the modified square wave signal to form a stimulation signal, which is transmitted to the percutaneous leads. In a preferred embodiment, each electrode in each percutaneous lead is individually addressable by the pulse generator. The pulse generator may change the polarity, and waveform of the stimulation signal sent to each electrode.

Pulse generator 616 is further connected to right signal lines 620, 621 and 622. Signal line 620 is connected to dmux 632 through ammeter 623. Signal line 621 is connected to dmux 632 through ammeter 624. Signal line 622 is connected to dmux 632 through ammeter 625.

Signal line 620 is further connected to electrode line 660 of percutaneous lead 603. Signal line 621 is further connected to electrode line 662 of percutaneous lead 603. Signal line 622 is further connected to electrode line 664 of percutaneous lead 603. Dmux 632 is further connected to voltage meter 631.

Voltage meter 631 is connected to CPU 602 through signal line 675. In operation, voltage measurements read by the voltmeter for the various configurations of the system are transmitted to the CPU through signal line 675.

CPU 602 is further connected to dmux 632 through control line 635. In operation, CPU 602, through control line 635, sets dmux 632 to connect one of signal lines 620, 621 or 622, selectively, to voltage meter 631. A first test setting connects signal line 620 and electrode line 660 to voltage meter 631. A second test setting connects signal line 621 and electrode line 662 to voltage meter 631. A third test setting connects signal line 622 and electrode line 664 to voltage meter 631.

Pulse generator 616 is further connected to signal lines 626, 627 and 628. Signal lines 626, 627 and 628 are further connected to relay 629. Relay 629 is further connected to dmux 630 through signal lines 671, 672 and 673. Relay 629 is further connected to electrode lines 666, 668 and 670 of percutaneous lead 601.

Dmux 630 is further connected to CPU 602 by control line 634. CPU 602 alternately places dmux 630 in one of three settings. In a first test setting, signal line 671 and electrode line 670 are connected to voltage meter 631 and system ground 633. In a second test setting, signal line 672 and electrode line 668 are connected to voltage meter 631 and system ground 633. In a third test setting, signal line 673 and electrode line 666 are connected to voltage meter 631 and system ground 633, as will be further described.

CPU 602 is further connected to relay 629 by control line 640. In operation, CPU 602 sets relay 629 to one of a stimulation setting or a test setting. In the stimulation setting, signal lines 626, 627 and 628 are connected to electrode lines 670, 668 and 666, respectively. In the test setting, relay 629, connects electrode lines 666, 668 and 670 signal lines 673, 672 and 671, respectively.

CPU 602 is further connected to relay 636 through control line 639. CPU 602, through control line 639, alternatively switches between the stimulation setting and the test setting. In the stimulation setting, return line 637, from pulse generator 616, is connected to ground line 638. In the test setting, return line 637 is disconnected from ground line 638. In a preferred embodiment, ground line 638 is connected to the titanium casing of the IPG, not shown.

When a resistivity test is conducted, the CPU individually processes through a set of electrode connections in a predetermined set of permutations. In each permutation, the current is measured through one of the ammeters and the voltage is measured across a selected pair of electrodes, as will be further described. In this example, each percutaneous lead is shown with three (3) independently addressable electrode lines, terminating in three (3) distal ring electrodes. Of course, alternate systems may have a greater or lesser number of electrodes and addressable control lines in the leads.

Referring them to FIG. 6B, an architecture drawing of master controller 680 will be further described.

Master controller 680 includes processor 682. Processor 682 is operatively connected to memory 686, communications interface 688 and keypad 684.

Instructions are resident in memory 686 which, when executed, allow processor 682 to carry out the functions required of the master controller.

Keypad 684 is typically a 12-button digital keypad which allows scrolling of information and entry of instructions from display 690.

Communications interface 688 operates to connect and send and receive information and data wirelessly to communications interface 606 of IPG 600.

Figure 7A:
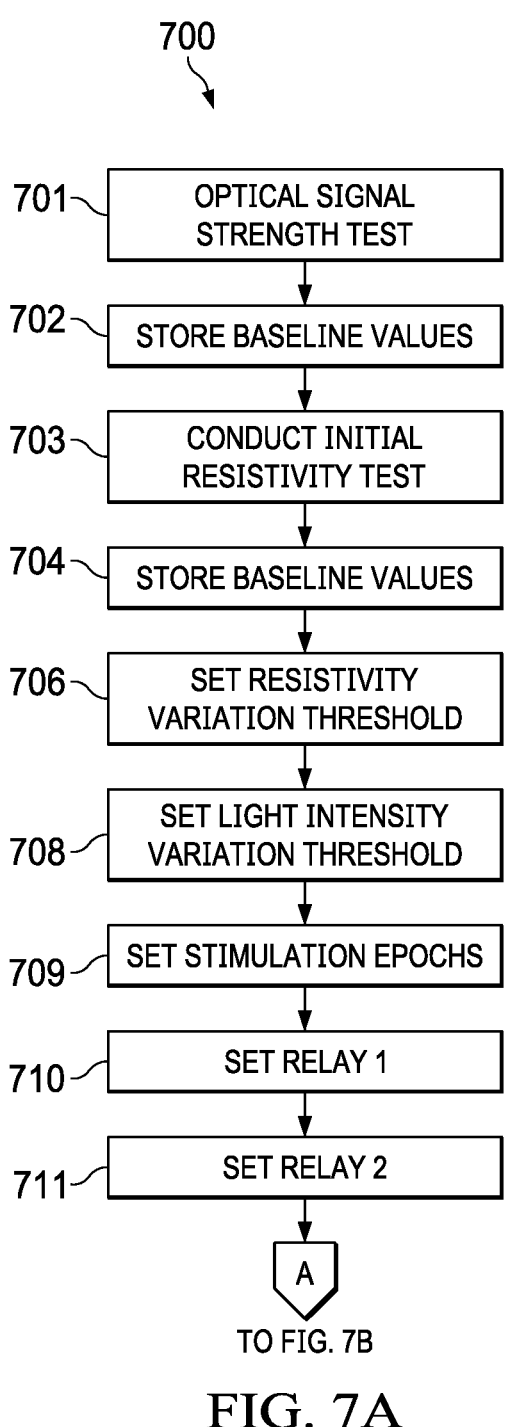
FIGS. 7A and 7B are a flowchart of a preferred method for sensing lead migration.
Figure 7B:
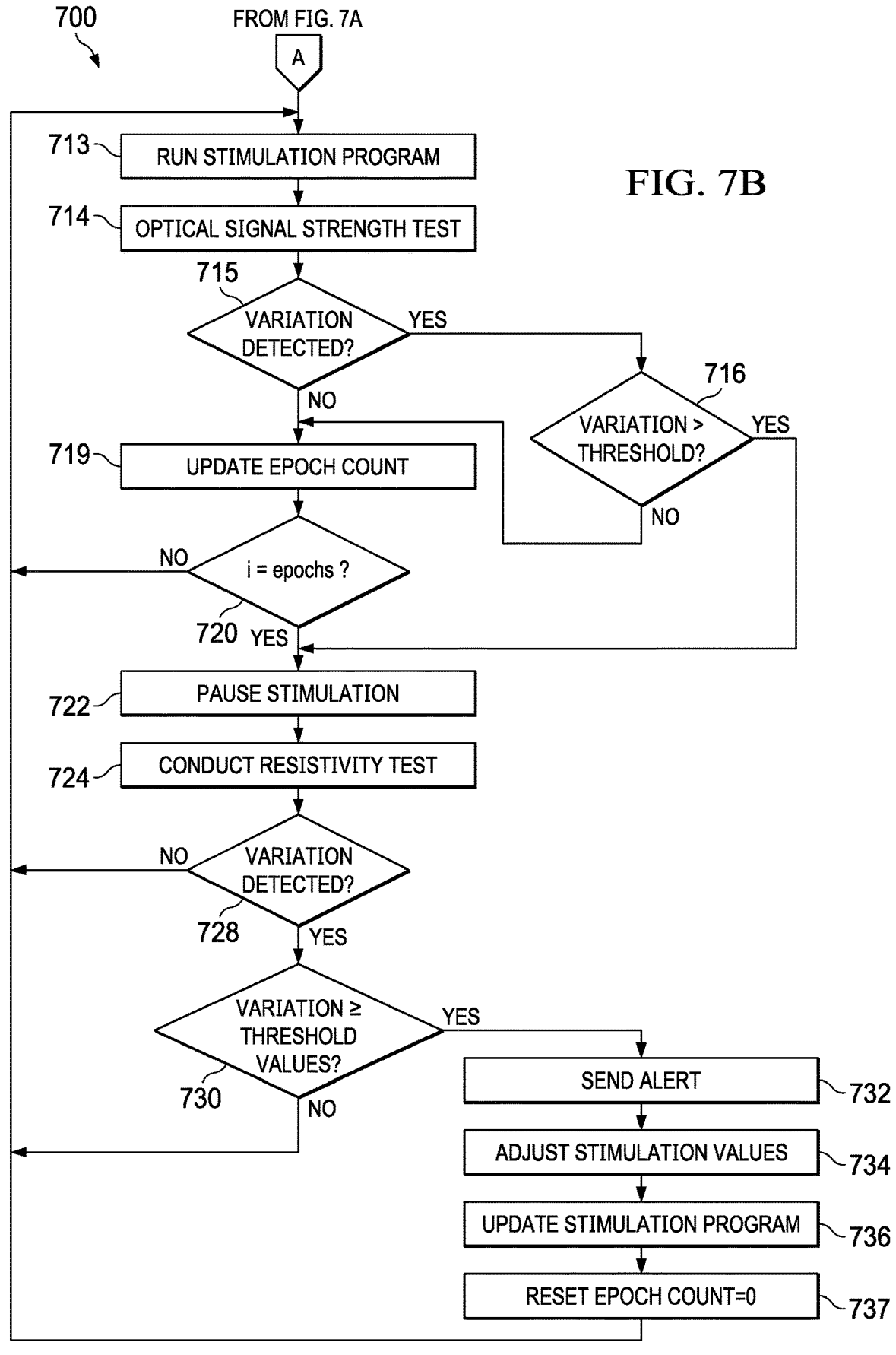

Referring then to FIGS. 7A, and 7B, preferred method 700 for dynamically adjusting the stimulation signal to reduce the effect of lead migration will be further described.

At step 701, an initial optics test is conducted, as will be further described. At step 702, a baseline light intensity value is stored in memory.

At step 703, an initial resistivity test is conducted, as will be further described.

At step 704, the baseline resistivity values are stored in memory. At step 706, a resistivity variation threshold is set. The resistivity variation threshold represents the maximum value of resistivity change that the system will tolerate before adjusting the stimulation waveform to compensate for lead migration to produce the desired stimulation at the focal point. In a preferred embodiment, the resistivity variation threshold is between about 10% and about 50%.

At step 708, the light intensity variation threshold is set. The light intensity variation threshold is the maximum amount the light intensity that can change before a resistivity test is conducted. In a preferred embodiment, the light intensity threshold is between about 10% and about 100%. At step 709, the number of stimulation epochs before a resistivity measurement is taken is set. In a preferred embodiment, the epoch duration is set to occur frequently to compensate for transitory sagittal movement of the leads. In a preferred embodiment, the number of stimulation epochs is between 100 and 10,000 cycles. In other embodiments, the epoch duration may be measured in increments of time. In this case, a preferred epoch duration may be in the range between 15 seconds and 2 hours. Of course, other epoch durations may be employed. In alternate embodiments, the epoch duration is set to occur infrequently to conserve power and account for permanent lead migration. In this case, the number of stimulation epochs is about 100,000 cycles or 1 day.

At step 710, relay 629 is placed in the stimulation setting by the CPU. At step 711, relay 636 is placed in the stimulation setting by the CPU.

At step 713, the stimulation program activates and runs for a single epoch. The optical modulator, IR emitter driver, optical signal processor, pulse modulator and pulse generator are activated by the CPU to produce stimulation signals at each of the right and left electrodes. At step 714, the system optically polls for light variation, as will be further described.

At step 715, the method determines whether or not a light variation is detected. In a preferred embodiment, the stored baseline photodiode voltage is compared to the test photodiode voltage. Preferably, variation is returned as "true" if more than about 10% change is detected. In another embodiment, variation is returned as "true" if more than between about 10% and about 20% change is detected. If so, the method proceeds to step 716. If not, the method proceeds to step 719.

At step 716, the method determines whether or not the light variation detected is greater than the light intensity variation threshold. If so, the method proceeds to step 722. If not, then the method proceeds to step 719.

At step 719, the epoch count is incremented.

At step 720, the method determines whether or not the stimulation has been conducted for the preset number of epochs. If not, the method returns to step 713. If so, the method proceeds to step 722.

At step 722, the stimulation signal is deactivated. At step 724, a resistivity test is conducted, as will be further described. At step 728, the resistivity values are compared to the baseline resistivity values to determine if a variation is present. In a preferred embodiment, a deviation between any two electrodes in the baseline resistivity matrix and the test resistivity matrix of about 10% or greater is considered a "true" condition. In another embodiment, a deviation of between about 10% and about 20% is considered a "true" condition. If not, the method returns to step 713. If so, then the method proceeds to step 730.

At step 730, the method determines whether or not the variation detected is greater than or equal to the threshold value set in step 706. If so, the method proceeds to step 732. If not, then the method returns to step 713.

At step 732, the system generates and transmits an alert to the communication interface queue indicating that the leads have migrated beyond the threshold value. At step 734, the stimulation values are adjusted to compensate for lead migration, as will be further described. At step 736, the stimulation program is updated to generate the new stimulation signal with the new values. At step 737, the epoch count is reset to zero. The method then returns to step 713.

Figure 7C:
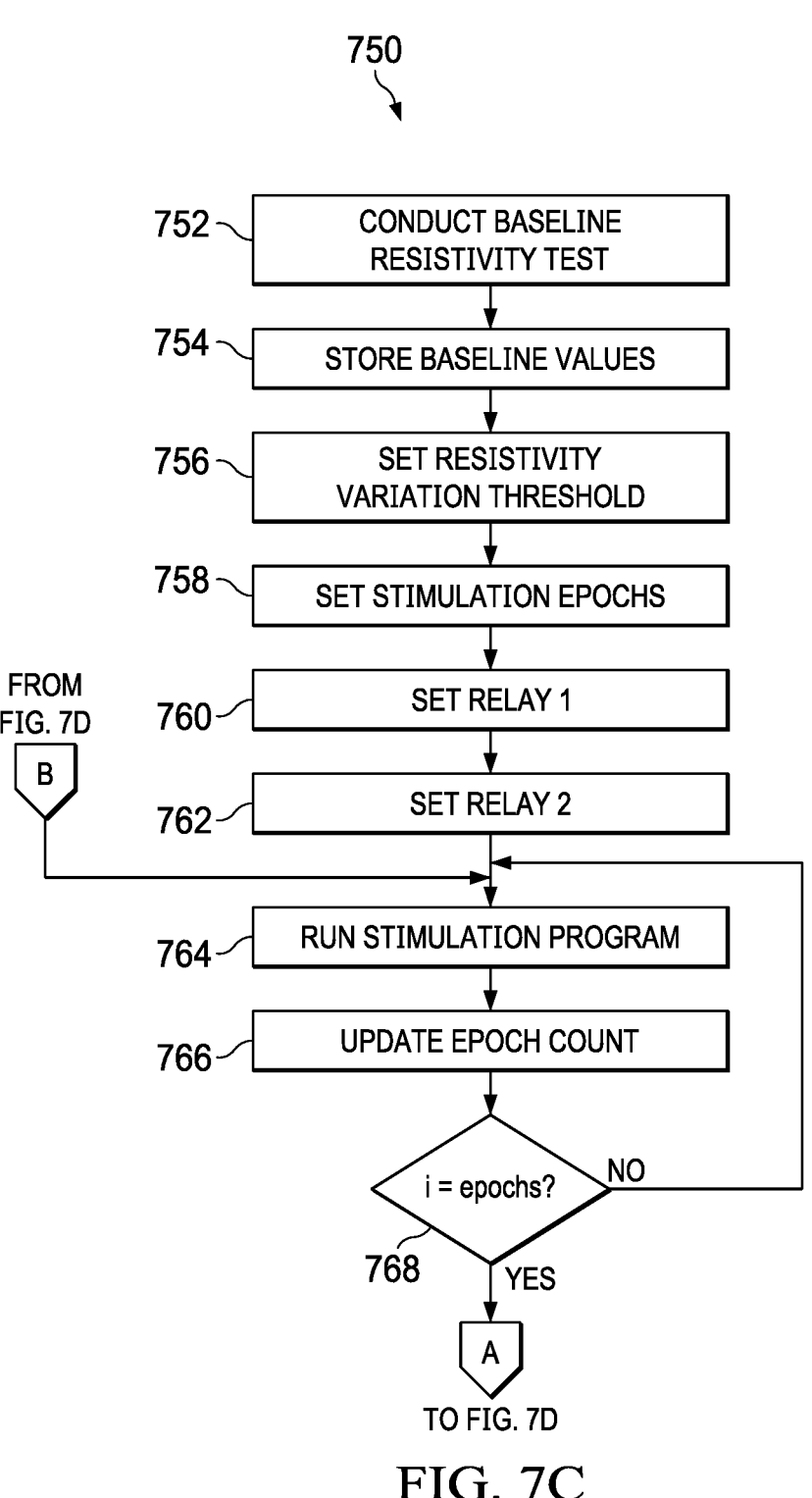
FIGS. 7C and 7D are a flowchart for an alternate method for sensing lead migration.
Figure 7D:
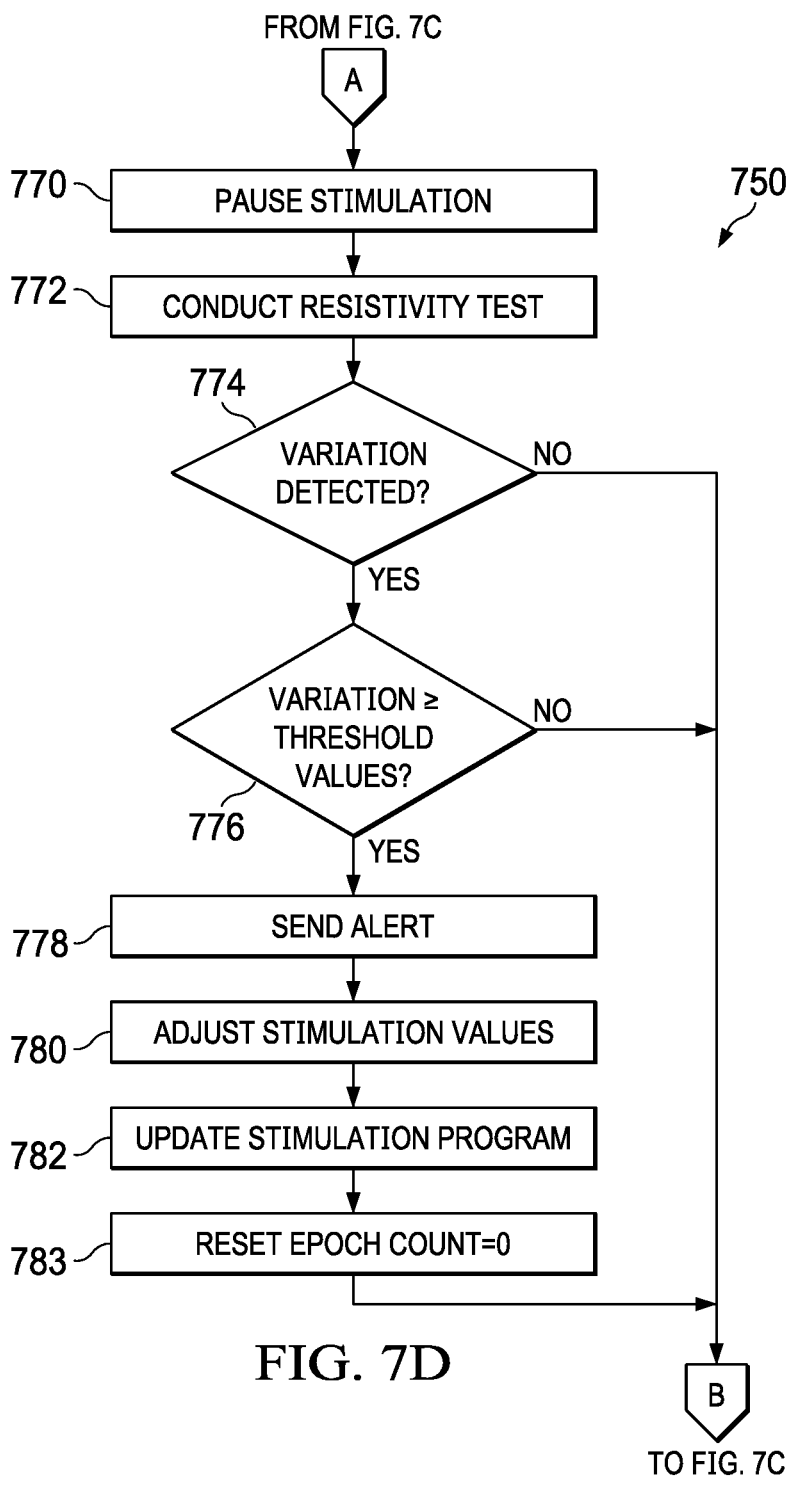

Referring then to FIGS. 7C and 7D, alternate method 750 for dynamically adjusting the stimulation signal to reduce the effect of lead migration will be further described.

At step 752, a baseline resistivity test is conducted, as will be further described.

At step 754, the baseline resistivity values are stored in memory. At step 756, a resistivity variation threshold is set, as previously described.

At step 758, the number of stimulation epochs before a resistivity measurement is taken is set, as previously described.

At step 760, relay 629 is placed in the stimulation setting by the CPU. At step 762, relay 636 is placed in the stimulation setting by the CPU.

At step 764, the stimulation program is activated and runs for a single epoch. The pulse modulator and pulse generator are activated by the CPU to produce stimulation signal at each of the right and left electrode leads. At step 766, the method updates the epoch count.

At step 768, the method determines whether or not the stimulation has been conducted for the preset number of epochs. If not, the method returns to step 764. If so, the method proceeds to step 770.

At step 770, the stimulation signal is deactivated. At step 772, a resistivity test is conducted, as will be further described. At step 774, the resistivity values are compared to the baseline resistivity values to determine if a variation is present, as previously described. If not, the method returns to step 764. If so, then the method proceeds to step 776.

At step 776, the method determines whether or not the variation detected is greater than or equal to the threshold value set in step 756. If so, the method proceeds to step 778. If not, then the method returns to step 764.

At step 778, the system generates and transmits an alert to the communication interface queue indicating that the leads have migrated beyond the threshold value. At step 780, the stimulation values are adjusted to compensate for lead migration, as will be further described. At step 782, the stimulation program is updated to generate the new stimulation signal with the new values. At step 783, the epoch count is reset to zero. The method then returns to step 764.

Figure 8:
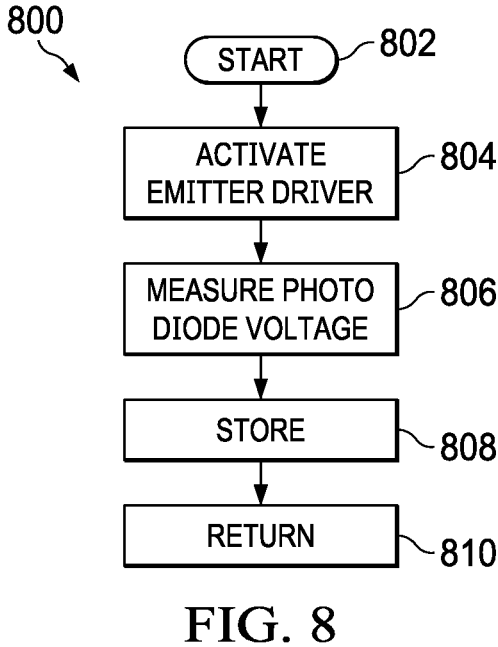
FIG. 8 is a flowchart of a preferred method of establishing an optical baseline.

Referring then to FIG. 8, method 800 of testing optical signal strength will be further described.

At step 802, the method begins. At step 804 IR emitter driver 610 is activated which sends a light pulse along optical fiber 613 which emits a pulse of light from the optical window on the right percutaneous fiber.

At step 806, the voltage across photodiode 612 is measured from an incoming light pulse along optical fiber 614. The light emitted from the optical window of the right fiber is received by the optical window of the left fiber and transmitted back to the photodiode. As the distance between the two percutaneous leads increases or decreases, the voltage across the photodiode will likewise increase or decrease, respectively, and proportionally.

At step 808, the photodiode voltage is stored in memory.

At step 810, the method returns.

Figure 9A:
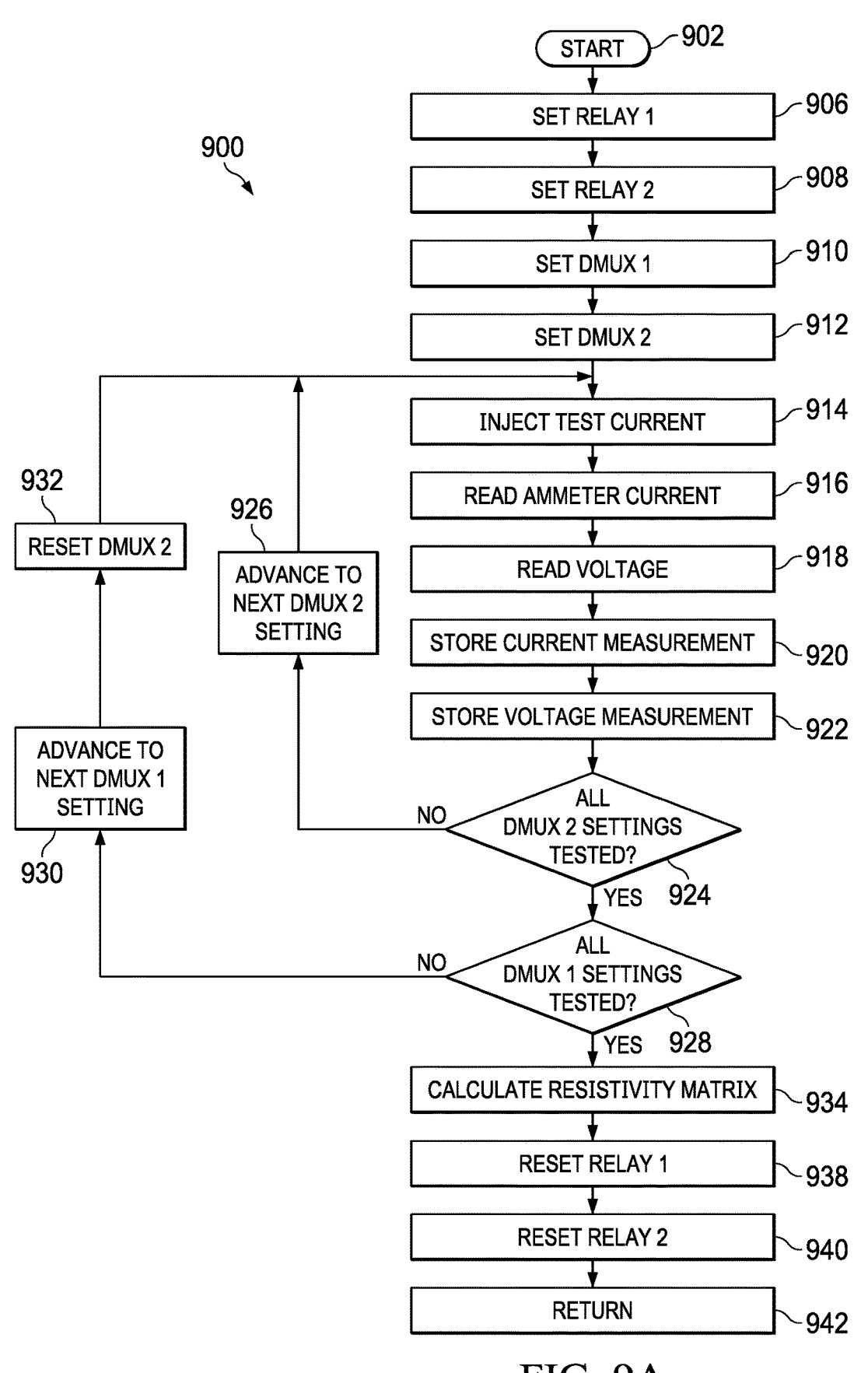
FIG. 9A is a flowchart of a preferred method of dynamically adjusting stimulation to accommodate for lead migration.

Referring then to FIGS. 6A and 9A, preferred method 900 of conducting a resistivity test will be further described.

At step 902, the method begins.

At step 906, relay 629 is set to its test state, by a test state signal, connecting electrode line 670 to signal line 671, electrode line 668 to signal line 672 and electrode line 666 to signal line 673.

At step 908, relay 636 is set to its test state, by a test state signal, disconnecting return line 637 from ground line 638.

At step 910, dmux 630 is set to its first test setting, by the test state signal, connecting line 671 to voltage meter 631 and system ground 633.

At step 912, dmux 632 is set to its first test setting, by the test state signal, connecting signal line 620 and electrode line 660 to voltage meter 631.

At step 914, the CPU injects a DC test current on signal line 620 which is transmitted to electrode line 660 of percutaneous lead 603 and voltage meter 631 through ammeter 623. The test current returns to ground through electrode line 670 of percutaneous lead 601.

At step 916, the current at ammeter 623 is measured.

At step 918, the voltage across voltage meter 631 is measured.

At step 920, the current measurement is stored in memory, in a test table indexed according to electrode placement, as will be further described.

At step 922, the voltage measurement is stored in memory, in the test table, indexed according to electrode placement, as will be further described.

At step 924, CPU determines whether or not all test settings of dmux 632 have been examined. If not, the method moves to step 926. If so, CPU moves to step 928.

At step 926, a CPU advances to the next test setting of dmux 632 and returns to step 914, where current is injected, and voltage and current readings are taken in the new configuration.

At step 928, the CPU determines whether or not all test settings of dmux 630 have been examined. If so, the CPU moves to step 934. If not, the CPU moves to step 930.

At step 930, CPU advances to the next test setting of dmux 630 and moves to step 932.

At step 932, the CPU resets dmux 632 to its first test setting and returns to step 914, where current is injected, and voltage and current readings are taken in the new configuration.

At step 934, the CPU calculates the resistivity values for the resistivity matrix, as will be further described.

At step 938, the CPU resets relay 629 to its stimulation state, by a stimulation state signal, connecting signal lines 626, 627 and 628 to electrode lines 670, 668 and 666, respectively.

At step 940, the CPU resets relay 636 to its stimulation state, by a stimulation state signal, connecting return line 637 to ground 638.

At step 942, the method returns.

Referring then to FIGS. 6A, 9B, 9C and 9D, a preferred method for calculating resistivity values according to electrode positions will be further described.

When dmux 630 is in its first test setting and dmux 632 is positioned in its first test setting, current is injected by electrode line 660. Voltage reading $V_{11}$ is then recorded between electrode lines 660 and 670. When dmux 632 is positioned in its second test setting, current is injected by electrode line 662. Voltage reading $V_{12}$ is recorded between electrode lines 662 and 670. When dmux 632 is in its third test setting, current is injected by electrode line 664. Voltage reading $V_{13}$ is recorded between electrode lines 664 and 670.

When dmux 630 is in its second test setting and dmux 632 is positioned in its first test setting, current is injected by electrode line 660. Voltage reading $V_{21}$ is recorded between electrode lines 660 and 668. When dmux 632 is positioned in its second test setting, current is injected by electrode line 662. Voltage reading $V_{22}$ is recorded between electrode lines 662 and 668. When dmux 632 is in its third test setting, current is injected by electrode line 664. Voltage reading $V_{23}$ is recorded between electrode lines 664 and 668.

When dmux 630 is in its third test setting and dmux 632 is positioned in its first test setting, current is injected by electrode line 660. Voltage reading $V_{31}$ is recorded between electrode lines 660 and 666. When dmux 632 is positioned in its second test setting, current is injected by electrode line 662. Voltage reading $V_{32}$ is recorded between electrode lines 662 and 666. When dmux 632 is positioned in its third test setting, current is injected by electrode line 664. Voltage reading $V_{33}$ is recorded between electrode lines 664 and 666.

The resistivity matrix is then calculated according to the following equation.

$$\begin{bmatrix} V_{11} & V_{12} & V_{13} \\ V_{21} & V_{22} & V_{23} \\ V_{31} & V_{32} & V_{33} \end{bmatrix} \div \begin{bmatrix} I_1 \\ I_2 \\ I_3 \end{bmatrix} = \begin{bmatrix} R_{11} & R_{12} & R_{13} \\ R_{21} & R_{22} & R_{23} \\ R_{31} & R_{32} & R_{33} \end{bmatrix}$$

Where:
$[V_{xy}]$ is the voltage measurement, indexed by d-mux test setting;
$I_1$ is the current measurement at ammeter 623;
$I_2$ is the current measurement at ammeter 624;
$I_3$ is the current measurement at ammeter 625;
$[R_{xy}]$ is the resistivity measurement indexed by d-mux test setting.

A preferred method of executing step 934 will now be further described.

To derive an adjustment to stimulation intensity, the following equations are employed.

$$[R_{LR\ Baseline}] - [R_{LR\ Test}] = [\Delta R_{LR}]$$

Where:

$R_{LR\ Baseline}$=the baseline resistivity matrix, indexed by d-mux test setting;

$R_{LR\ Test}$=the test resistivity matrix, indexed by d-mux test setting; and, $\Delta R_{LR}$=the resulting difference matrix, indexed by d-mux test setting.

The percentage change between the baseline resistivity matrix and the test resistivity matrix is then calculated according to the following equation.

$$\frac{[\Delta R_{LR}]}{R_{LR\ Baseline}}[\% \ change_{LR}]$$

Where:
$\Delta R_{LR}$ is the change between the baseline and the test resistivity matrices;
$R_{LR\ Baseline}$ is the baseline resistivity matrix; and,
$\% \ change_{LR}$ is a percentage change between the baseline resistivity matrix and the test resistivity matrix.

In a preferred embodiment, the stimulation signal amplitude is increased for each electrode by the same percentage as the resistivity changes in the percent change LR matrix.

Figure 10:
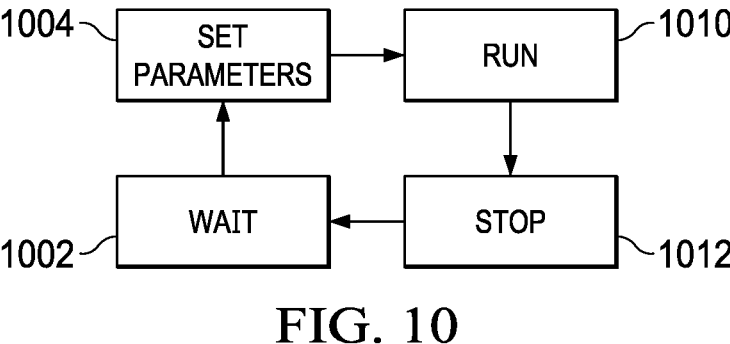
FIG. 10 is a preferred controller state chart.

Referring then to FIG. 10, the various states of the IPG controller will be described. At "wait" state 1002, the CPU enters a waiting posture and continually polls for an I/O signal. Upon receipt of an I/O signal, the CPU immediately sends all data in the communications queue to the communications interface and enters "set parameter" state 1004. At set parameters state 1004, values for epoch length, threshold light intensity and threshold resistivity are received from the communications interface and passed to the CPU. The system then moves to run state 1010. In run state 1010, the CPU executes method 700 and periodically polls the communication interface.

If a "stop" signal is received by the communications interface, then the CPU moves to stop state 1012. At stop state 1012, the CPU terminates all active routines and returns to wait state 1002.

The invention claimed is:

1. A spinal stimulation system comprising:
a controller, having a processor and a memory;
a set of flexible leads, each lead of the set of flexible leads having an optical fiber and an array of electrodes, operatively connected to the controller; and
the memory containing a set of instructions, that when executed, cause the spinal stimulation system to:
optically determine a first set of positional data using the optical fiber;
optically determine a second set of positional data using the optical fiber;
electrically determine a third set of positional data using the array of electrodes;
derive a first comparison between the first set of positional data and the second set of positional data; and
if the first comparison is greater than a first threshold value then:
conduct a resistivity test, using the array of electrodes, to acquire a fourth set of positional data;
derive a second comparison between the third set of positional data and the fourth set of positional data;
if the second comparison is greater than a second threshold value, then:

determine a set of stimulation currents based on the second comparison; and direct the set of stimulation currents to the array of electrodes.

2. The spinal stimulation system of claim 1 wherein the set of instructions further comprises instructions that, when executed, cause the spinal stimulation system to:

wait a predetermined number of stimulation signal epochs before executing the step of optically determining the second set of positional data.

3. The spinal stimulation system of claim 2 wherein the set of instructions further comprises instructions that, when executed, causes the spinal stimulation system to:

conduct a baseline resistivity test to acquire a baseline set of positional data.

4. The spinal stimulation system of claim 1 wherein the set of instructions further comprises instructions that, when executed, cause the spinal stimulation system to:

pause the set of stimulation currents if the first comparison is greater than the first threshold value.

5. The spinal stimulation system of claim 1 further comprising:

a light emitter, operatively connected to the controller and a first optical fiber of a first lead of the set of flexible leads;

a light detector, operatively connected to the controller and a second optical fiber of a second lead of the set of flexible leads; and, wherein the step of optically determining the first set of positional data further comprises:

generating, by the light emitter, an incident light beam on the first optical fiber;

receiving, by the light detector, a reflected light beam on the second optical fiber; and, measuring an intensity difference between the incident light beam and the reflected light beam.

6. The spinal stimulation system of claim 1 wherein the step of determining the set of stimulation currents further comprises:

calculating a variation matrix based on the second comparison; and if an element of the variation matrix is greater than a threshold value:

calculating the set of stimulation currents based on the variation matrix.

7. The spinal stimulation system of claim 6 further comprising:

a second relay system, operatively connected to a pulse generator, the controller and a ground connection.

8. The spinal stimulation system of claim 7 wherein:

a first demultiplexer system and a voltmeter are further operatively connected to the ground connection.

9. The spinal stimulation system of claim 1 further comprising:

a pulse generator, operatively connected to the controller;

a first relay system, operatively connected to the controller, the pulse generator and a first set of electrodes of the array of electrodes;

a first demultiplexer system, operatively connected to the controller, the first relay system and a voltmeter;

a second demultiplexer system, operatively connected to the controller, a second set of electrodes of the array of electrodes and the voltmeter; and, a set of ammeters, operatively connected to the pulse generator and the second set of electrodes of the array of electrodes.

10. The spinal stimulation system of claim 9 wherein the set of instructions further comprises instructions that when executed cause the spinal stimulation system to:

set the first relay system to a test state position;

set the first demultiplexer system to a first position of a first set of positions;

set the second demultiplexer system to a first position of a second set of positions;

inject a test current, to the array of electrodes, based on the first position of the first set of positions and the first position of the second set of positions;

read a first ammeter current from the set of ammeters;

read a first voltage from the voltmeter;

determine if all positions of the second set of positions have been tested;

if all positions of the second set of positions have not been tested then advancing to a next position of the second set of positions and returning to the step of injecting;

if all positions of the second set of positions have been tested then determining if all positions of the first set of positions have been tested;

if all positions of the first set of positions have not been tested then advancing to a next position of the first set of positions and resetting the second demultiplexer system to the first position of the second set of positions and returning to the step of injecting; and if all positions of the first set of positions have been tested, then calculating a resistivity matrix based on the first ammeter current and the first voltage.

11. The spinal stimulation system of claim 10 wherein the set of instructions further comprises instructions that, when executed, cause the spinal stimulation system to:

configure a test state by sending a test state signal to the first relay system, the first demultiplexer system and the second demultiplexer system.

12. The spinal stimulation system of claim 11 wherein the test state further comprises:

a first operative connection between the voltmeter, the first demultiplexer system, the first relay system and the first set of electrodes; and, a second operative connection between the voltmeter, the second demultiplexer system, the set of ammeters, the second set of electrodes and the pulse generator.

13. The spinal stimulation system of claim 12 wherein the test state further comprises a switchable connection between a system ground and the first set of electrodes.

14. The spinal stimulation system of claim 11 wherein the set of instructions further comprises instructions that, when executed, cause the spinal stimulation system to:

configure a stimulation state, by sending a stimulation state signal to the first relay system, the first demultiplexer system, and the second demultiplexer system.

15. The spinal stimulation system of claim 14 wherein the stimulation state further comprises:

a third operative connection between the pulse generator, the first relay system and the first set of electrodes;

a fourth operative connection between the pulse generator and the second set of electrodes.

16. The spinal stimulation system of claim 15 wherein the stimulation state further comprises a second switchable connection between the pulse generator and a system ground.

17. The spinal stimulation system of claim 14 wherein the set of instructions further comprises instructions that, when executed, cause the spinal stimulation system to:

toggle between the test state and the stimulation state based on an optical difference trigger signal.

* * * * *